(12) United States Patent
Wollin

(10) Patent No.: US 10,151,820 B2
(45) Date of Patent: *Dec. 11, 2018

(54) APPARATUS AND METHOD FOR MAPPING AND MEASUREMENT OF SPATIALLY AND TEMPORALLY DISTRIBUTED INDUCED SMALL PHASE DEVIATIONS IN MAGNETIC RESONANCE UTILIZING DECONVOLUTION

(71) Applicant: Wollin Ventures, Inc., Sarasota, FL (US)

(72) Inventor: Ernest Wollin, Sarasota, FL (US)

(73) Assignee: Wollin Ventures, Inc., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/725,714

(22) Filed: Oct. 5, 2017

(65) Prior Publication Data

US 2018/0045803 A1 Feb. 15, 2018

Related U.S. Application Data

(63) Continuation of application No. 14/400,851, filed as application No. PCT/US2013/032594 on Mar. 15, 2013, now Pat. No. 9,791,535.

(Continued)

(51) Int. Cl.
*G01R 33/565* (2006.01)
*A61B 5/055* (2006.01)
(Continued)

(52) U.S. Cl.
CPC ........ *G01R 33/56563* (2013.01); *A61B 5/055* (2013.01); *G01R 33/243* (2013.01); *G01R 33/34076* (2013.01); *G01R 33/3678* (2013.01); *G01R 33/565* (2013.01); *G01R 33/5608* (2013.01); *G01R 33/56536* (2013.01)

(58) Field of Classification Search
CPC ............ G01R 33/56563; G01R 33/243; G01R 33/34076; G01R 33/3678; G01R 33/5608; G01R 33/565; G01R 33/56536; A61B 5/055

See application file for complete search history.

(56) References Cited

U.S. PATENT DOCUMENTS 4,602,348 A 7/1986 Hart
4,665,366 A 5/1987 Macovski
(Continued)

OTHER PUBLICATIONS

Bernstein, M.A., King, K.F., Zhou, X.J., "Handbook of MRI Pulse Sequences", Elsevier Academic Press, Oxford, U.K., 2004, Ch 13.5, (e.g. Figure 13.34).

(Continued)

*Primary Examiner* — Gregory H Curran
(74) *Attorney, Agent, or Firm* — Foley & Lardner LLP

(57) ABSTRACT

Phase variations of the transverse magnetization in magnetic resonance induced by superimposed physical phenomenae or by intrinsic deviations of the main magnetic B0 field are separated from Feature Space set by demodulation and deconvolution, either by electrical circuits or by equivalent computational methods, permitting mapping and measurement of these induced phase variations independent of Feature Space.

3 Claims, 6 Drawing Sheets

Related U.S. Application Data

(60) Provisional application No. 61/746,420, filed on Dec. 27, 2012, provisional application No. 61/647,717, filed on May 16, 2012.

(51) Int. Cl.

| | |
|---|---|
| *G01R 33/36* | (2006.01) |
| *G01R 33/24* | (2006.01) |
| *G01R 33/34* | (2006.01) |
| *G01R 33/56* | (2006.01) |

(56) References Cited

U.S. PATENT DOCUMENTS

| | | | |
|---|---|---|---|
| 5,086,275 | A | 2/1992 | Roemer |
| 5,412,322 | A | 5/1995 | Wollin |
| 5,757,187 | A | 5/1998 | Wollin |
| 5,757,951 | A | 5/1998 | Tuy |
| 6,127,825 | A | 10/2000 | Goto |
| 6,774,629 | B2 | 8/2004 | Miyoshi |
| 6,853,191 | B1 | 2/2005 | Miller et al. |
| 7,403,006 | B2 | 7/2008 | Garwood et al. |
| 7,852,084 | B2 | 12/2010 | Zhai et al. |
| 8,082,127 | B2 | 12/2011 | Ruhm |
| 8,200,309 | B2 | 6/2012 | Wollin |
| 2005/0052182 | A1 | 3/2005 | Wollin |
| 2005/0093545 | A1 | 5/2005 | Yoshizawa |
| 2005/0114038 | A1 | 5/2005 | Szyperski et al. |
| 2006/0226840 | A1 | 10/2006 | Chmielewski et al. |
| 2010/0085048 | A1 | 4/2010 | Bouchard et al. |
| 2010/0106008 | A1* | 4/2010 | Harvey ............ G01R 33/34046 600/422 |
| 2012/0076435 | A1 | 3/2012 | Sharma et al. |

OTHER PUBLICATIONS

Cho, Z.; Jones, J.P.; Singh, M., "Foundations of Medical Imaging", John Wiley & Sons, New York, 1993.

Chow, L. et al. "Investigation of MR signal modulation due to magnetic fields from neuronal currents in the adult human optic nerve and visual cortex." Magnetic Resonance Imaging, 24 (2006), pp. 681-691.

Dorf, R.C., "The Electrical Engineering Handbook", IEEE CRC Press, Boca Raton, Florida, 1993, Ch. 63.

Extended European Search Report dated May 4, 2016 in related European Appl. 13790096.5 (12 pgs.).

Hahn, E.L. Phys. Rev. 80, 580, (1950).

International Search Report and Written Opinion for PCT/US2013/032594; dated Jun. 17, 2013; 8 pages.

Kovalchuk. Advances in Magnetic Resonance Electrical Impedance Mammography; Apr. 4, 2008; Retrieved from ProQuest Dissertations and Theses: <URL: http://search.proguestcom/docview/304463513/fulltextPDF/13E338F81472F361FA9/1?accountid=142944>; pp. 83-89.

Kumar, A; Welti, D; Ernst, R.R.: J.Magn Reson. 18, 69 (1975).

Liang, Z.; Lauterbur, P.C., "Principles of Magnetic Resonance Imaging" IEEE Press, New York, 2000, p. 99, Ch.3.

Mansfield, P; J. Phys. C10, L55 (1977).

Noll, D. et al. "Homodyne Detection in Magnetic Resonance Imaging." IEEE Transactions on Medical Imaging, vol. 10, No. 2, Jun. 1991, pp. 154-163.

Stark, DD and Bradley, WG: Magnetic Resonance Imaging, (St. Louis, Mosby) Ch. 70 "Functional Magnetic Resonance Imaging" 1999.

Notice of Allowance dated Jun. 12, 2017 in parent U.S. Appl. No. 14/400,851.

\* cited by examiner

APPARATUS AND METHOD FOR MAPPING AND MEASUREMENT OF SPATIALLY AND TEMPORALLY DISTRIBUTED INDUCED SMALL PHASE DEVIATIONS IN MAGNETIC RESONANCE UTILIZING DECONVOLUTION

CROSS-REFERENCE TO RELATED PATENT APPLICATIONS

This application claims the benefit and the priority to U.S. Provisional Patent Application Ser. No. 61/647,717, filed May 16, 2012, and U.S. Provisional Ser. No. 61/746,420, filed Dec. 27, 2012. The foregoing provisional applications are hereby incorporated by reference in their entirety.

BACKGROUND OF THE INVENTION

This invention pertains to magnetic resonance applications where focal phase deviations of the transverse magnetization are produced e.g.: by applied electrical energy, as in Magnetic Resonance Electrical Impedance Mammography, by metabolicaly induced susceptibility variations, as in Functional Magnetic Resonance Brain Imaging, or by local deviations in the intensity of the main magnetic $B_0$ field.

Suppression of dephasing produced by local deviations in the main magnetic field by successive radio frequency (r.f.) pulses was discovered by Hahn. [Hahn, E. L. Phys. Rev. 80, 580, (1950)] (which is hereby incorporated by reference in its entirety). Image formation in magnetic resonance imaging can be performed by multi-dimensional Fourier methods [Kumar, A; Welti, D; Ernst, R. R.: J.Magn Reson. 18, 69 (1975)] (which is hereby incorporated by reference in its entirety), by single sweep "echo-planar" methods [Mansfield, P; J. Phys. C10, L55 (1977)](which is hereby incorporated by reference in its entirety), or by combinations and permutations thereof.

Phase sensitive detection is well-known in radio communication [Dorf, R. C., "The Electrical Engineering Handbook", IEEE CRC Press, Boca Raton, Fla., 1993, Ch. 63] (which is hereby incorporated by reference in its entirety) and in magnetic resonance image formation [Liang, Z.; Lauterbur, P. C., "Principles of Magnetic Resonance Imaging" IEEE Press, New York, 2000, p. 99, Ch. 3] (which is hereby incorporated by reference in its entirety), as are spatially orthogonal coil sets and generalizations to bird-cage multi-phase coils [Cho, Z.; Jones, J. P.; Singh, M., "Foundations of Medical Imaging", John Wiley & Sons, New York, 1993](which is hereby incorporated by reference in its entirety). Phase sensitive detection resolves the received signal into real even (cosine) and imaginary odd (sine) components with respect to the magnetic resonance (MR) machine radio frequency (r.f.) generator creating magnitude and phase maps as in Miyoshi (U.S. Pat. No. 6,774,629) (which is hereby incorporated by reference in its entirety). Phase difference reconstruction to produce a phase difference map is known prior art in magnetic resonance imaging requiring manipulation of two or more independently acquired complex data sets. [Bernstein, M. A., King, K. F., Zhou, X. J., "Handbook of MRI Pulse Sequences", Elsevier Academic Press, Oxford, U. K., 2004, Ch 13.5, (e.g. FIG. 13.34)] (which is hereby incorporated by reference in its entirety).

OBJECTS OF THE INVENTION

The object of this invention is to obtain a single data set by deconvolution of the spatially and temporally distributed phase deviations of the transverse magnetization produced by various electrical and thermodynamic phenomenae that are superimposed on various applications of magnetic resonance to a sample under evaluation so as to permit spatial mapping and physical quantization of these superimposed phenomenae within the sample under evaluation. The transverse magnetization is the xy component of the net magnetization vector at right angles to the main magnetic field produced by a magnetic resonance device. An additional object of this invention is to simultaneously image these phase deviations and the original native image in magnetic resonance imaging without complex arc tangent processing or subtracting multiple complex data sets acquired from multiple data acquisition sequences.

SUMMARY OF THE INVENTION

The received electrical output from the existing magnetic resonance device receiver coil sets is combined electrically by analog circuits, or digitized and combined mathematically by digital computational methods, with a specified phase-shifted Larmor frequency output of the $B_1$ magnetic resonance device radio frequency (r.f.) generator, separately producing the original native data set and the original native data set multiplied everywhere by the data set of the spatially and temporally ordered induced phase deviations, as a spatial Fourier transform, allowing deconvolution into the original native data set and the data set of the spatially and temporally ordered induced phase deviations, permitting efficient spatial localization of, and analysis of, the physical phenomenae that produced these phase deviations, e.g. breast cancer conductivity or deoxygenation of hemoglobin by neuronal activity, or permitting suppression of phase variations, e.g., in magnetic resonance imaging.

DETAILED DESCRIPTION OF THE PREFERRED EMBODIMENTS

Figure 1:
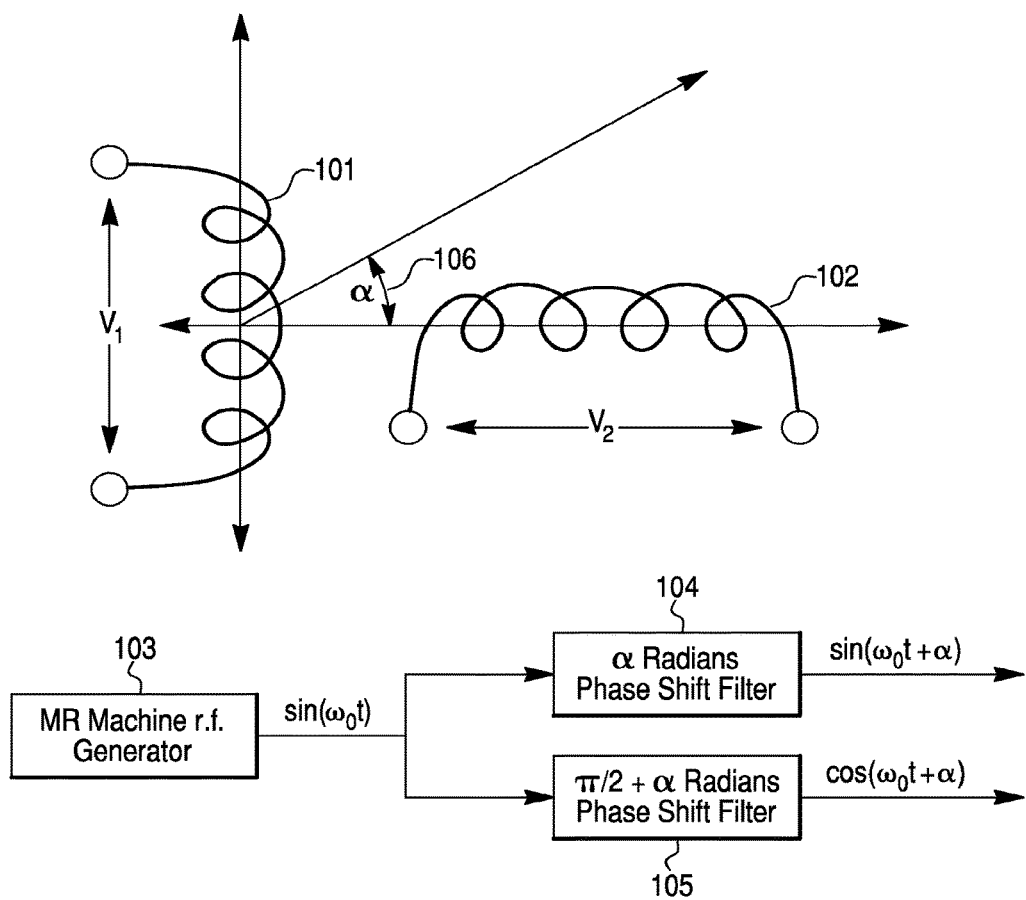
FIG. 1 is a diagram illustrating the output of a magnetic resonance machine receiver coil set and the output of a magnetic resonance machine master radio frequency (r.f.) generator both as it originates from the generator and as it passes through a phase shifting network.

Unless otherwise specified, "a" or "an" means "one or more."

As a general example, image formation in magnetic resonance is achieved by application of impulsive phase-encoding "magnetic gradients" and/or by application of continuous frequency-encoding "magnetic gradients" in various permutations, to a sample under evaluation, which can be generalized as $$[M] = e^{j\omega_0 t}\left[\int_F m_{(x,y,z)} d^{jk_x xt}(e^{jn(\Delta\kappa_y)y} e^{jm(\Delta\kappa_z)z}) dx\right]_{n,m}$$

Where [M] is the total transverse magnetization available to the receiver coil set, m is the transverse magnetization at each position (x, y, z) within a sample under evaluation, Kx is the temporal rate of change of the spatial frequency in radians per meter per second produced by the frequency encode gradient in the x-direction, $\Delta\kappa$ is the spatial frequency in radians per meter produced by the phase encode gradients applied impulsively in the y and z directions, n and m are the phase encoding steps of the gradients applied impulsively in the y and z direction, $\omega_0$ is the Larmor frequency, and F is the field of view, all as is known in the art. As noted above, the transverse magnetization is the xy component of the net magnetization vector at right angles to the main magnetic field produced by a magnetic resonance device.

The sample under evaluation may be any human tissue such as a human breast or a human brain, or any other material suitable for analysis by a magnetic resonance machine.

Focal deviations in spatial phase $\varphi$ of the transverse magnetization can be produced at each position (x, y, z) of the sample under evaluation, e.g., by focal variations in susceptibility, as produced in Functional Magnetic Brain Imaging (as explained, for example, by Stark, D D and Bradley, W G: Magnetic Resonance Imaging, (St. Louis, Mosby) Ch. 70 "Functional Magnetic Resonance Imaging" (1999), which is hereby incorporated by reference in its entirety), variations in transverse current density as produced in Magnetic Resonance Electrical Impedance Mammography (as explained in U.S. Pat. No. 8,200,309, which is herein incorporated by reference in its entirety), or by focal variations in magnetic field intensity, as produced, e.g., by chemical shift, magnetization transfer, or temperature variations, all as known in prior art.

These focal phase deviations produce a complex spatially distributed transverse magnetization function m' in local Gaussian complex planes transverse everywhere to the solenoidal main magnetic field $B_0$ whose imaginary jy axis is defined as collinear everywhere to the $B_1$ Larmor r.f. applied magnetic field $$m' = me^{j\varphi}$$

at each position (x,y,z) within the sample under evaluation. For small deviations in phase $\varphi$, this complex spatially distributed transverse magnetization function can be approximated as $$m' = me^{j\varphi} = m(\cos\varphi + j\sin\varphi) \cong m + m\varphi e^{j\frac{\pi}{2}}$$

producing two components of the total transverse magnetization available to the receiver coil set, one equivalent to [M], the total transverse magnetization of the original feature space, and a second component [M'] in spatial quadrature with [M] equal to the product of the transverse magnetization m at each point of this feature space everywhere with $\varphi$, the local deviation in phase, producing an Aberrational Feature Space [M']. The resulting total transverse spatial magnetization $$[M_T] = \left[\left[Me^{j\omega_0 t}\right] + \left[M'e^{j(\omega_0 t + \frac{\pi}{2})}\right]\right]$$

produces a voltage V in a coil of the spatially distributed quadrature coil set of $$V = Pe^{j\omega_0 t} + Qe^{j(\omega_0 t + \frac{\pi}{2})}$$

in complex function notation.

[M] and [M'] are orthogonal in space but not in time. P and Q are voltages representing the temporal development of the spatial Fourier transform of [M] and [M'], respectively. P and Q are orthogonal in time, but not in space. For clarity of exposition, the equivalent real function notation yields $$V_1 = P \sin \omega_0 t + Q \cos \omega_0 t$$

as the voltage induced in quadrature coil A, and $$V_2 = P \cos \omega_0 t - Q \sin \omega_0 t$$

as the voltage induced in quadrature coil B. Then, in matrix notation, $$\begin{bmatrix} V_1 \\ V_2 \end{bmatrix} = \begin{bmatrix} \sin\omega_0 t & \cos\omega_0 t \\ \cos\omega_0 t & -\sin\omega_0 t \end{bmatrix} \times \begin{bmatrix} P \\ Q \end{bmatrix}$$

and by Cramer's rule $$P = -\begin{vmatrix} V_1 & \cos\omega_0 t \\ V_2 & -\sin\omega_0 t \end{vmatrix}; \quad Q = -\begin{vmatrix} \sin\omega_0 t & V_1 \\ \cos\omega_0 t & V_2 \end{vmatrix}$$

$$P = V_1 \sin\omega_0 t + V_2 \cos\omega_0 t;$$
$$Q = -V_2 \sin\omega_0 t + V_1 \cos\omega_0 t$$

Thus, both the spatial Fourier transform of Feature Space (P) and of the Aberrational Feature Space (Q) can be recovered directly, without suppressing harmonics, simultaneously and independently from one set of observations by multiplying the output voltage of each quadrature coil by sin $\omega_0 t$ or by cos $\omega_0 t$ phase-shifted voltages obtained from the magnetic resonance (MR) machine radio frequency (r.f.) generator and adding or subtracting the voltages so produced, as specified. The spatial Fourier transform of Feature Space (P) represents the original native data set output by the magnetic resonance machine after evaluation of the sample under evaluation without the induction of the spatially and temporally ordered phase deviations. The spatial Fourier transform of Aberrational Feature Space (Q) represents the data set of the product everywhere of the original native data set and the induced spatially and temporally ordered phase deviations.

Preferably, the same coil set is used for excitation and reception to minimize phase drift and spatial distortion. The MR machine can be a conventional MRI device, which provides magnetic resonance images of a sample. Example MRI devices are described in the inventor's prior U.S. Pat. Nos. 5,412,322 and 5,757,187, incorporated by reference herein in their entirety. Further, images may be generated using the spatial Fourier transform of Feature Space (P) and Aberrational Feature Space (Q). The images may be generated by a computing device or the MR machine itself and may subsequently be displayed or computationally analyzed.

Figure 2:
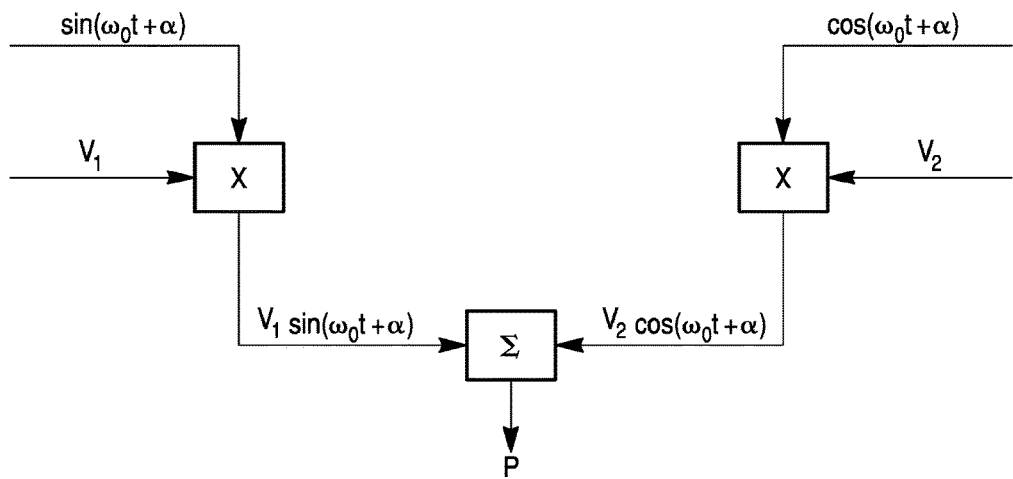
FIG. 2 is a diagram illustrating the output signals of FIG. 1 multiplied and then summed so as to produce the spatial Fourier transform of the original native data set.
Figure 3:
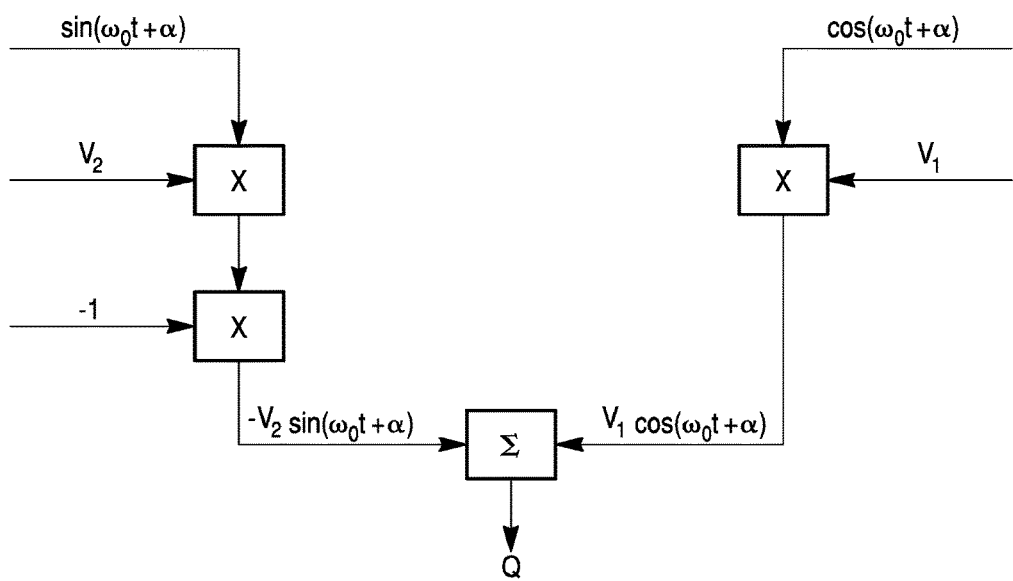
FIG. 3 is a diagram illustrating the output signals of FIG. 1 multiplied and then summed so as to produce the spatial Fourier transform of the product of the original native data set and the data set of the spatially and temporally ordered induced phase deviations, which spatial Fourier transform is the convolution of the spatial Fourier transform of the original native data set and the spatial Fourier transform of the spatially and temporally ordered induced phase deviations.

FIGS. 1 through 3 illustrate an embodiment of the present invention including a quadrature coil set as described above. In particular, FIG. 1 includes a magnetic resonance (MR) machine receiver quadrature coil set including quadrature coil A 101 and quadrature coil B 102. Quadrature coil B 102 is on an axis rotated an angle $\alpha$ 106 with respect to an axis orthogonal to the solenoidal $B_0$ main magnetic field. Quadrature coil A 101 is also rotated an angle $\alpha$, though because its axis is orthogonal to that of coil B 102's axis, the axis of coil A 101 is an angle ($\pi/2+\alpha$) radians from the axis orthogonal to the solenoidal $B_0$ main magnetic field noted above for coil B 102. The MR receiver coil set (coil A 101 and coil B 102) outputs electrical output when the magnetic resonance machine (not illustrated) evaluates a sample under evaluation. FIG. 1 also illustrates receiving phase-shifted voltages $\cos(\omega_0 t+\alpha)$ and $\sin(\omega_0 t+\alpha)$ obtained from the MR machine radio frequency (r.f.) generator 103 which are phase shifted such that the $\sin(\omega_0 t)$ signal from the MR machine r.f. generator 103 is phase shifted using an $\alpha$ radians phase shift filter 104 and a ($\pi/2+\alpha$) radians phase shift filter 105 to produce the $\sin(\omega_0 t+\alpha)$ and $\cos(\omega_0 t+\alpha)$ signals, respectively, as shown. The phase shifting network embodied in FIG. 1 as phase shift filter 104 and phase shift filter 105 may be implemented using analog circuits or may be implemented by digitizing the output of the MR machine r.f. generator 103 and shifting the output using digital computational methods.

FIG. 2 illustrates the output signals of FIG. 1 multiplied and then summed so as to produce the spatial Fourier transform of Feature Space (P) (representing the original native data set relating to the sample under evaluation). In particular, as illustrated in FIG. 2, $\cos(\omega_0 t+\alpha)$ is multiplied with $V_2$, and $\sin(\omega_0 t+\alpha)$ is multiplied with $V_1$. The result of those multiplications $V_1 \sin(\omega_0 t+\alpha)$ and $V_2 \cos(\omega_0 t+\alpha)$ are summed to produce the spatial Fourier transform of Feature Space (P). The multiplication and summation operations illustrated by FIG. 2 may be accomplished using analog circuits or may be accomplished by digitizing the output signals of FIG. 1 (or by receiving digital output signals from FIG. 1) and then using digital computational techniques.

FIG. 3 illustrates the output signals of FIG. 1 multiplied and then summed so as to produce the spatial Fourier transform of Aberrational Feature Space (Q). In particular, as illustrated in FIG. 3, $\cos(\omega_0 t+\alpha)$ is multiplied with $V_1$, and $\sin(\omega_0 t+\alpha)$ is multiplied with $-V_2$. The result of those multiplications $-V_2 \sin(\omega_0 t+\alpha)$ and $V_1 \cos(\omega_0 t+\alpha)$ are summed to produce the spatial Fourier transform of Aberrational Feature Space (Q) (representing the product everywhere of the original native data set and the induced spatially and temporally ordered phase deviations). The multiplication and summation operations illustrated by FIG. 3 may be accomplished using analog circuits or may be accomplished by digitizing the output signals FIG. 1 (or by receiving digital output signals from FIG. 1) and then using digital computational techniques.

Thus, the embodiment illustrated in FIGS. 1 through 3 recovers both the spatial Fourier transform of Feature Space (P) (representing the original native data set relating to the sample under evaluation) and the spatial Fourier transform Aberrational Feature Space (Q) (representing the product everywhere of the original native data set and the induced spatially and temporally ordered phase deviations) directly, without suppressing harmonics, simultaneously and independently from one set of observations.

Figure 4:
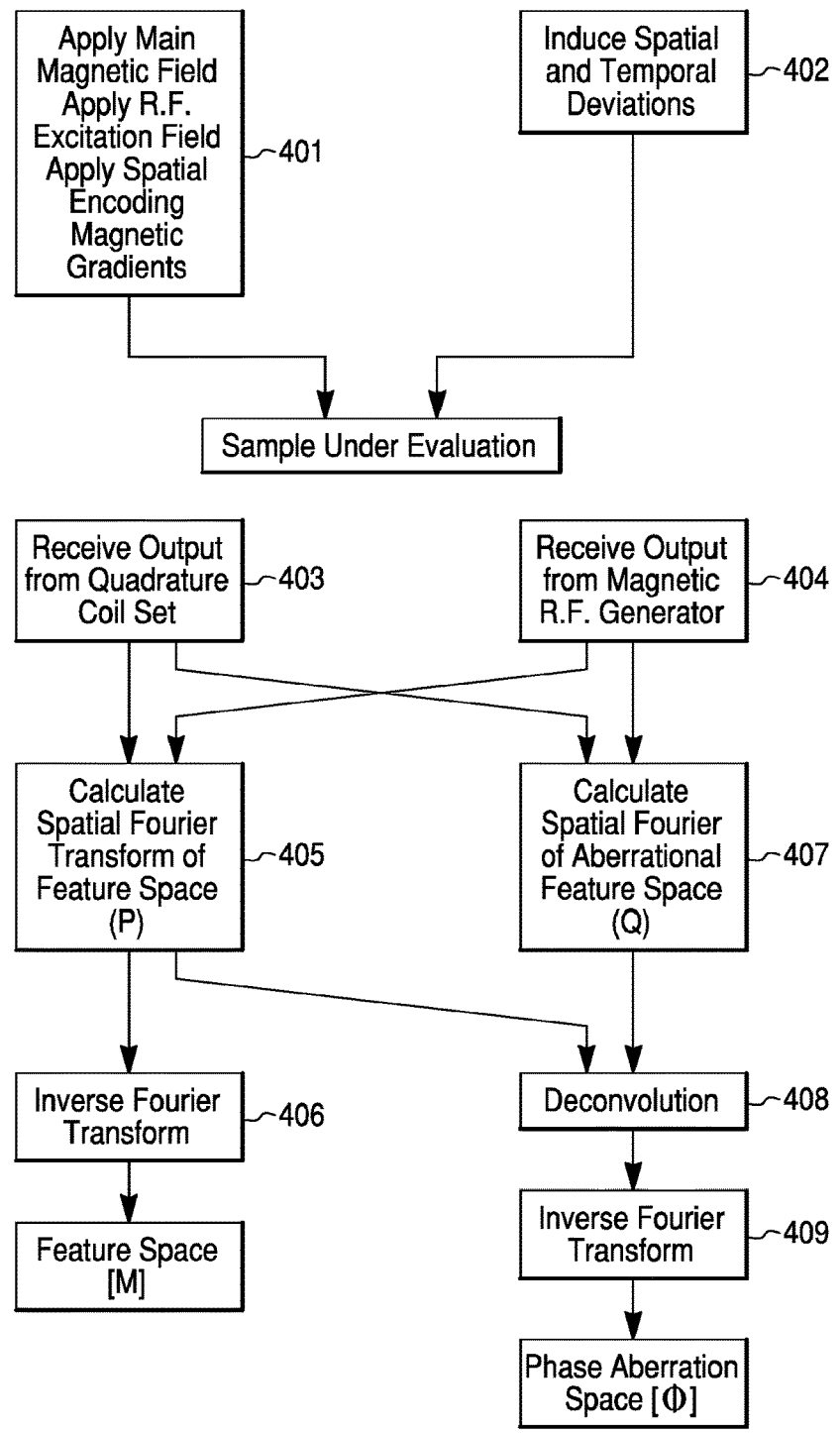
FIG. 4 is a flowchart illustrating a method for identifying spatially and temporally distributed phase deviations within a sample under evaluation, according to one embodiment.

FIG. 4 is a flowchart illustrating a method for identifying spatially and temporally distributed phase deviations within a sample under evaluation, according to one embodiment. The method of FIG. 4 includes the application of the main magnetic field, r.f. excitation field, and spatial encoding magnetic gradients to the sample under evaluation in the magnetic resonance machine in step 401. In step 402, spatially and temporally ordered phase deviations of the transverse magnetization within the sample under evaluation are induced. In step 403, output is received from the quadrature coil set as a first voltage and a second voltage ($V_1$ and $V_2$). In step 404, output of a magnetic resonance machine radio frequency generator is received, and then phase-shifted to generate first and second phase-shifted voltages. The magnetic resonance machine generator functions as a master oscillator In step 405, the spatial Fourier transform of Feature Space (P) (representing the original native data set relating to the sample under evaluation) is calculated. The details of that calculation are provided in FIG. 2, and the disclosure of the Specification that accompanies FIG. 2. In step 406, an inverse Fourier Transform is applied to spatial Fourier transform of Feature Space (P) to generate Feature Space [M] which is the original native data set. In step 407, the spatial Fourier transform of Aberrational Feature Space (Q) (representing the product everywhere of the original native data set and the induced spatially and temporally ordered phase deviations) is calculated. The details of that calculation are provided in FIG. 3, and the disclosure in the Specification that accompanies FIG. 3. In step 408, a deconvolution algorithm is performed on the spatial Fourier transform of Aberrational Feature Space (Q) and the spatial Fourier transform of Feature Space (P) to generate the Fourier transform of Phase Aberration Space [Φ]. In step 409, an inverse Fourier Transform is applied to the Fourier transform of Phase Aberration Space [Φ] (result of step 408) to generate Phase Aberration Space [Φ]. The operations illustrated with respect to FIG. 4 may be accomplished using analog circuits or may be accomplished using digital computing techniques.

Figure 5:
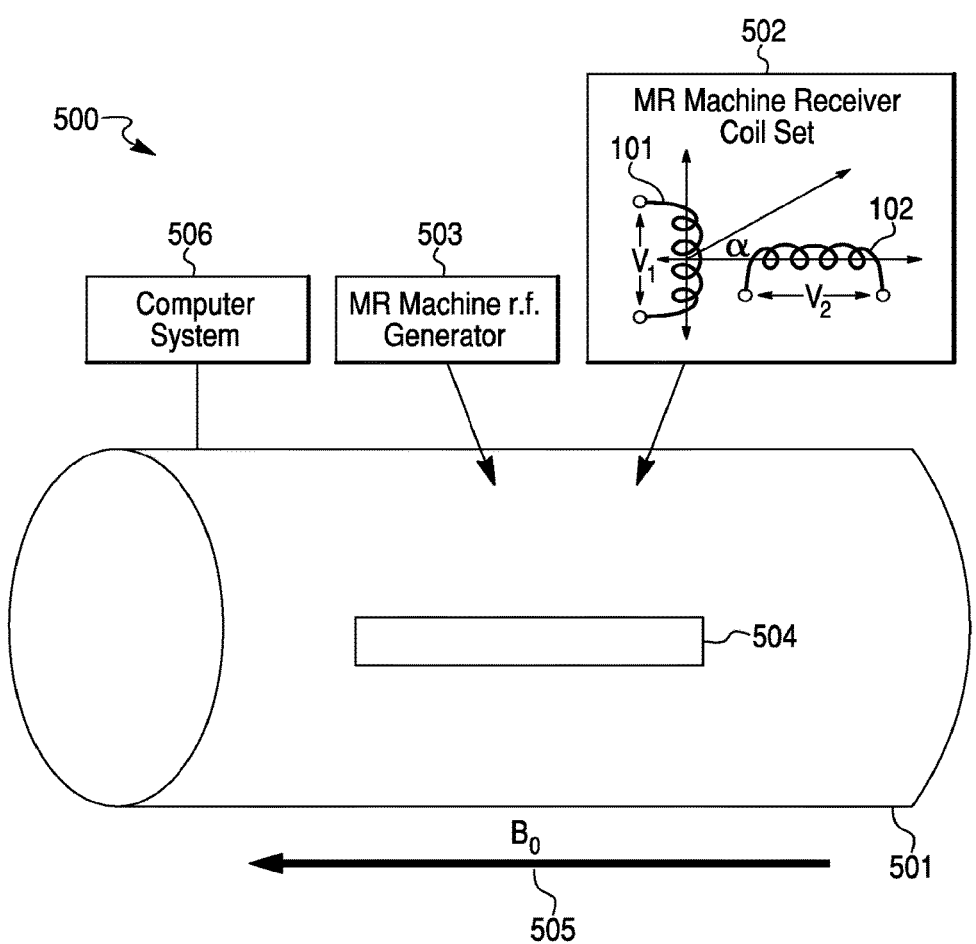
FIG. 5 is a diagram illustrating a system for identifying spatially and temporally distributed phase deviations within a sample under evaluation, according to one embodiment.

FIG. 5 illustrates a system for identifying spatially and temporally distributed phase deviations within a sample under evaluation 500, according to one embodiment. The system includes a magnetic resonance machine 501. The magnetic resonance machine 501 includes a quadrature coil set 502 that includes a quadrature coil A 101 and a quadrature coil B 102. The embodiment of FIG. 5 may be used with other types of coils such as a coil set with only one coil or a birdcage coil of multiple orthogonal elements. The magnetic resonance machine 501 also includes a magnetic resonance machine radio frequency generator 503. Within the magnetic resonance machine 501 is a sample under evaluation 404. The magnetic resonance machine 501 applies a main magnetic field 505 to the sample under evaluation 504. The magnetic resonance machine 501 may also apply an r.f. excitation field, and spatial encoding magnetic gradients. Additionally, the system 500 includes an induction component (not illustrated) that is configured to induce spatially and temporally ordered phase deviations of the transverse magnetization within the sample under evaluation 504. In some embodiments, the spatially and temporally ordered phase deviations may be induced without an induction component by metabolicaly induced susceptibility variations, as in Functional Magnetic Resonance Brain Imaging, or by local deviations in the intensity of the main magnetic $B_0$ field 505. The system further includes a computer system 506. The computer system 506 is configured to collect output from the quadrature coil set 502 and the magnetic resonance machine radio frequency generator 503 and calculate the spatial Fourier transform of Feature Space (P) (representing the original native data set relating to the sample under evaluation) and the spatial Fourier transform of Aberrational Feature Space (Q) (representing the product everywhere of the original native data set and the induced spatially and temporally ordered phase deviations), as detailed in FIGS. 2 and 3 and their accompanying disclosure from the Specification. The computer system 506 is also configured to perform deconvolution and inverse Fourier Transforms to recover Feature Space [M] and Phase Aberration Space [Φ], as detailed in FIG. 4 and its accompanying disclosure.

The same result can be obtained from a single coil without quadrature coils using a π/2 radian phase shifting electrical filter if the phase shift produced by the filter is essentially constant over the bandwidth of the induced voltages P and Q. The voltage induced in a single receiver coil by the transverse magnetization of Larmor r.f. carrier frequency $e^{j\omega_0 t}$ rotating in the (x, jy) Gaussian plane in space is amplitude modulated by the low temporal frequency function $P_{(t)}$ and can be written as $P_{(t)}\sin \omega_0 t$.

The voltage induced in a single receiver coil by the transverse magnetization of Larmor r.f. carrier frequency $e^{j(\omega_0 t+\pi/2)}$ rotating in the (x, jy) Gaussian plane in space is amplitude modulated by the low temporal frequency function $Q_{(t)}$ and can be written as $Q_{(t)}\sin(\omega_0 t+\pi/2)$.

This yields a total output voltage of $$V_1 = P_{(t)}\sin \omega_0 t + Q_{(t)}\cos \omega_0 t$$

Passing $V_1$ through an electrical filter shifting temporal phase by π/2 radians at the carrier Larmor r.f. frequency $\omega_0$ yields $$V_2 = P_{(t)}\sin(\omega_0 t + \pi/2) + Q_{(t)}\cos(\omega_0 t + \pi/2)$$

$$V_2 = P_{(t)}\cos \omega_0 t - Q_{(t)}\sin \omega_0 t$$

Again, in matrix notation $$\begin{bmatrix} V_1 \\ V_2 \end{bmatrix} = \begin{bmatrix} \sin\omega_0 t & \cos\omega_0 t \\ \cos\omega_0 t & -\sin\omega_0 t \end{bmatrix} \times \begin{bmatrix} P \\ Q \end{bmatrix}$$

and, by Cramer's rule $$P = -\begin{vmatrix} V_1 & \cos\omega_0 t \\ V_2 & -\sin\omega_0 t \end{vmatrix}; \quad Q = -\begin{vmatrix} \sin\omega_0 t & V_1 \\ \cos\omega_0 t & V_2 \end{vmatrix}$$

$$P = V_1 \sin\omega_0 t + V_2 \cos\omega_0 t;$$

$$Q = -V_2 \sin\omega_0 t + V_1 \cos\omega_0 t$$

Thus, multiplying $V_1$ and $V_2$ by $\sin \omega_0 t$ or by $\cos \omega_0 t$ phase-shifted voltages from the MR machine r.f. generator and adding or subtracting as specified yields P, the original Feature Space Fourier transform function and Q, the Aberrational Feature Space Fourier transform function. This can be achieved with two passive r.f. phase shifting filters, four double balanced modulators, the reference Larmor frequency from the MR machine r.f. generator, and two summing amplifiers.

Figure 6:
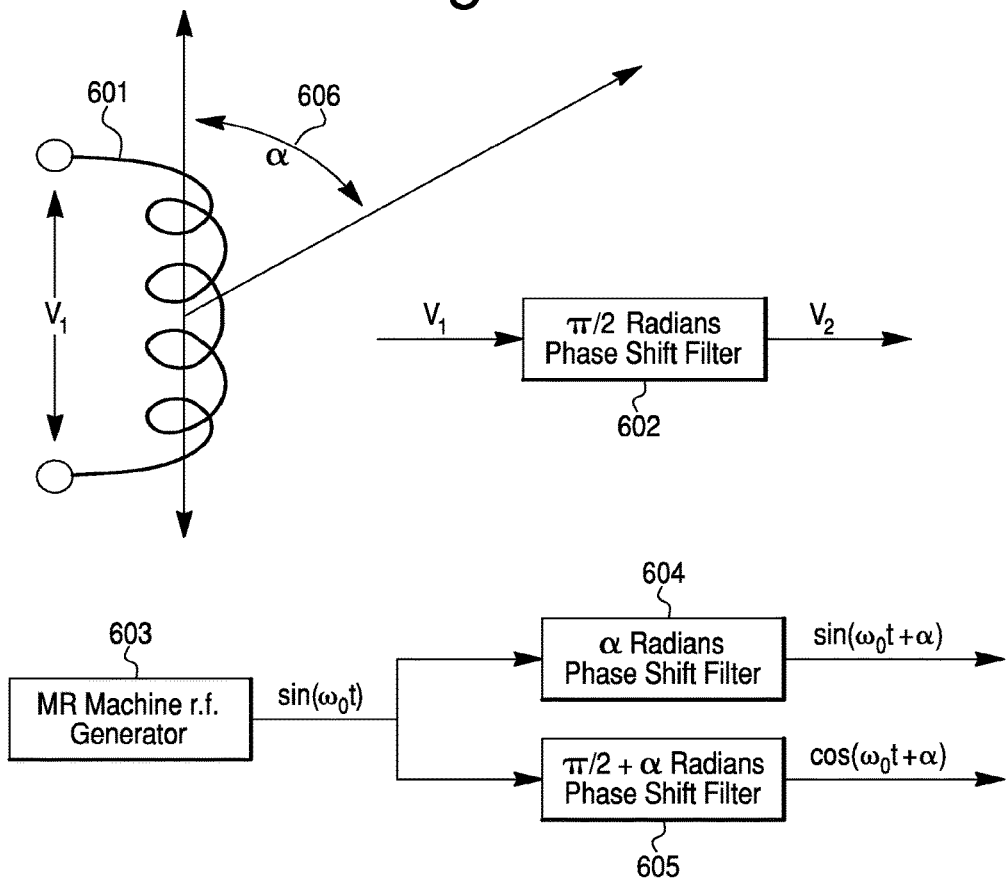
FIG. 6 is a diagram illustrating the output of a magnetic resonance machine receiver coil with an accompanying phase shift filter and the output of a magnetic resonance machine master radio frequency (r.f.) generator both as it originates from the generator and as it passes through a phase shifting network.

FIG. 6 is a diagram illustrating the output of a magnetic resonance machine receiver coil with an accompanying phase shift filter and the output of a magnetic resonance machine master radio frequency (r.f.) generator both as it originates from the generator and as it passes through a phase shifting network. In particular, FIG. 6 is an embodiment of a magnetic resonance (MR) machine receiver coil including a single coil A 601. FIG. 6 further includes a π/2 phase shift filter 602 which takes a first voltage from quadrature coil A 601 and produces a second voltage. Quadrature coil A is on an axis rotated an angle α 606 with respect to an axis orthogonal to the solenoidal $B_0$ main magnetic field. The MR receiver coil outputs electrical output when the magnetic resonance machine (not illustrated) evaluates a sample under evaluation. FIG. 6 also illustrates receiving phase-shifted voltages $\cos(\omega_0 t+\alpha)$ and $\sin(\omega_0 t+\alpha)$ obtained from the MR machine radio frequency (r.f.) generator 603 which are phase shifted such that the $\sin(\omega_0 t)$ signal from the MR machine r.f. generator 603 is phase shifted using an α radians phase shift filter 604 and a (π/2+α) radians phase shift filter 605 to produce the sin $(\omega_0 t+\alpha)$ and $\cos(\omega_0 t+\alpha)$ signals, respectively, as shown. The phase shifting network embodied in FIG. 6 as phase shift filter 604 and phase shift filter 605 may be implemented using analog circuits or may be implemented by digitizing the output of the MR machine r.f. master oscillator 603 and shifting the output using digital computational methods.

Based on the first and second voltage output as shown in FIG. 6, the processes described with respect to FIGS. 2 and 3 can be used to recover both the spatial Fourier transform of Feature Space (P) (representing the original native data set relating to the sample under evaluation) and the spatial Fourier transform Aberrational Feature Space (Q) (representing the product everywhere of the original native data set and the induced spatially and temporally ordered phase deviations) directly, without suppressing harmonics, simultaneously and independently from one set of observations.

This can be extended to a birdcage coil of multiple orthogonal sets, each set having area vectors rotated by α radians with respect to an axis orthogonal to the solenoidal $B_0$ main magnetic field. Though not shown pictorially, the birdcage coil embodiment uses multiple MR receiver coil sets (coil A 101 and coil B 102) as shown in FIG. 1, where the angle α 106 between the axis of coil B 102 and some axis orthogonal to the solenoidal $B_0$ is different for each MR receiver coil set. As noted previously, Quadrature coil A 101 is also rotated an angle α, though because its axis is orthogonal to that of coil B 102's axis, the axis of coil A 101 is an angle (π/2+α) radians from the axis orthogonal to the solenoidal $B_0$ main magnetic field noted above for coil B 102. Then, $$V_1 = P\sin(\omega_0 t + \alpha) + Q\cos(\omega_0 t + \alpha)$$
$$= P(\sin\omega_0 t \cdot \cos\alpha + \cos\omega_0 t \cdot \sin\alpha) + Q(\cos\omega_0 t \cdot \cos\alpha - \sin\omega_0 t \cdot \sin\alpha)$$

$$V_2 = P\sin[(\omega_0 t + \pi/2) + \alpha] + Q\cos[(\omega_0 t + \pi/2) + \alpha]$$
$$= P[\sin(\omega_0 + \pi/2) \cdot \cos\alpha + \cos(\omega_0 + \pi/2) \cdot \sin\alpha] +$$
$$Q[\cos(\omega_0 + \pi/2) \cdot \cos\alpha - \sin(\omega_0 + \pi/2) \cdot \sin\alpha]$$

-continued $$\sin(\omega_0 t + \pi/2) = \cos(\omega_0 t);$$

$$\cos(\omega_0 t + \pi/2) = -\sin(\omega_0 t)$$

$$V_2 = P(\cos\omega_0 t \cdot \cos\alpha - \sin\omega_0 t \cdot \sin\alpha) + Q(-\sin\omega_0 t \cdot \cos\alpha - \cos\omega_0 t \cdot \sin\alpha)$$

In matrix notation $$\begin{bmatrix} V_1 \\ V_2 \end{bmatrix} = \begin{bmatrix} \sin\omega_0 t\cos\alpha + \cos\omega_0 t\sin\alpha & \cos\omega_0 t\cos\alpha - \sin\omega_0 t\sin\alpha \\ \cos\omega_0 t\cos\alpha - \sin\omega_0 t\sin\alpha & -\sin\omega_0 t\cos\alpha - \cos\omega_0 t\sin\alpha \end{bmatrix} \times \begin{bmatrix} P \\ Q \end{bmatrix}$$

By Cramer's rule $$P = \frac{V_1(-\sin\omega_0 t\cos\alpha - \cos\omega_0 t\sin\alpha) - V_2(\cos\omega_0 t\cos\alpha - \sin\omega_0 t\sin\alpha)}{-(\sin\omega_0 t\cos\alpha + \cos\omega_0 t\sin\alpha)^2 - (\cos\omega_0 t\cos\alpha - \sin\omega_0 t\sin\alpha)^2}$$

$$= \frac{-V_1(\sin(\omega_0 t + \alpha)) + V_2(\cos(\omega_0 t + \alpha))}{-(\sin(\omega_0 t + \alpha))^2 - (\cos(\omega_0 t + \alpha))^2}$$

$$P = V_1 \sin(\omega_0 t + \alpha) + V_2 \cos(\omega_0 t + \alpha).$$

Similarly, $$Q = V_1 \cos(\omega_0 t + \alpha) - V_2 \sin(\omega_0 t + \alpha)$$

The output Q is the Fourier transform of [M'], the Aberrational Feature Space, which is the product everywhere of the Feature Space [M], with the Phase Aberration Space [Φ]. The output P is the Fourier transform of the Feature Space [M]. Therefore, we have:

[M']=[[M][Φ]]

and, $Q=\tilde{f}[M']$ and, $\tilde{f}[M']=\tilde{f}[[M][\Phi]]$ so, $Q=\tilde{f}[[M][\Phi]]$ The Fourier transform of a product is the convolution of the Fourier transform of each of the elements of the product, permitting separation by deconvolution of the measured Fourier transform of the Aberrational Feature Space into the independently measured Fourier transform of the Feature Space and into the required Fourier transform of the Phase Aberration space, as follows:

$Q=\tilde{f}[[M][\Phi]]=\tilde{f}[M]*\tilde{f}[\Phi]$ so, $Q=P*\tilde{f}[\Phi]$

This allows recovery of the Phase Aberration Space [Φ] using a deconvolution and an inverse Fourier transform as follows:

$\tilde{f}[\Phi]=Q^{*-1}P$ so, $\Phi=\tilde{f}^{-1}(Q^{*-1}P)$

This shows that, since P and Q are independently measured outputs of the system, [Φ] can be obtained by deconvolution and computing the inverse Fourier transform.

In the foregoing analysis the Phase Aberration Space [Φ] is treated as distributed in space but not as varying with time. If the Phase Aberration varies rapidly in time with respect to the "read time" of the receiver of the magnetic resonance device, this will create a local Fourier shift of the Phase Aberration Space, exaggerating high spatial frequency boundaries, as would occur with focal aberrations in transverse current flux density in Magnetic Resonance Electrical Impedance Mammography (U.S. Pat. No. 8,200,309B2 to Wollin). If the local phase aberration varies slowly in time, as would occur with magnetic susceptibility variations in space in functional magnetic resonance brain imaging, this slowly varying phase aberration will disproportionately distort the low spatial frequency central components of K-space exaggerating low frequency contrast variations. Therefore, both the demarcation of boundaries of regions of phase aberration and the contrast between regions of phase aberration will be affected differently, depending on the temporal frequency of the local phase variations.

Figure 7:
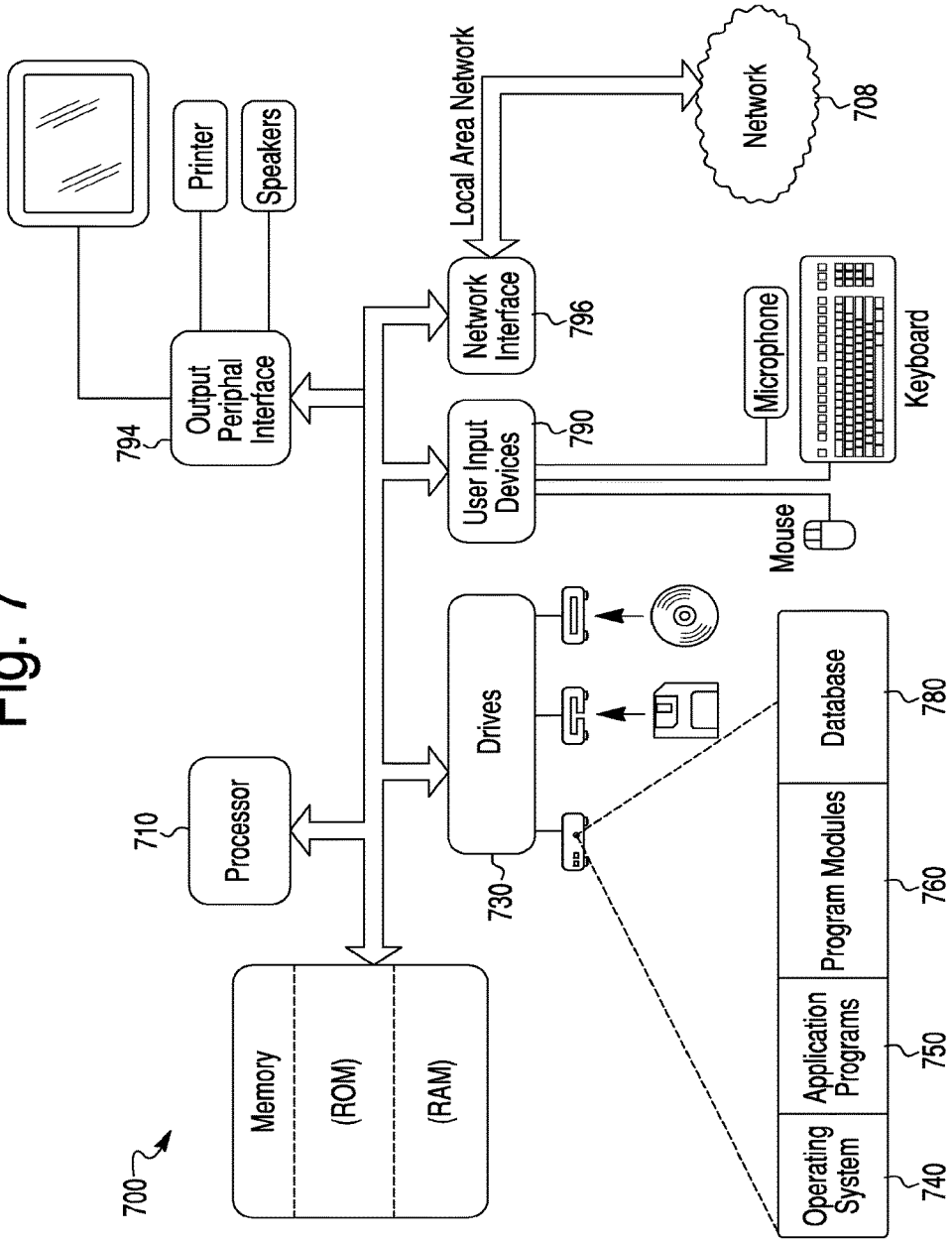
FIG. 7 presents an exemplary computing system or mobile computing system for implementing embodiments.

As noted above, the calculations and operations of FIGS. 1 through 4 may be performed with analog circuits, or may be performed digitally. FIG. 7 presents an exemplary computing system for implementing embodiments. The system 700 of FIG. 7 includes a computer 700, including a processor 710, and memory 720. The system may include one or more drives 730. The drives 730 and their associated computer storage media, provide storage of computer readable instructions, data structures, program modules and other data for the computer 700. Drives 730 can store an operating system 740, application programs 750, program modules 760, and database 780. The drives 730 may include CDROM or DVD drives, hard disk drives, flash drives, or other non-volatile electronic storage devices. The system 700 may further include user input devices 790 through which a user may enter commands and data. Input devices can include an electronic digitizer, a microphone, a keyboard and pointing device, commonly referred to as a mouse, trackball or touch pad. Other input devices may include a joystick, game pad, satellite dish, scanner, or the like.

These and other input devices can be connected to processor 710 through a user input interface that is coupled to a system bus, but may be connected by other interface and bus structures, such as a parallel port, game port or a universal serial bus (USB). The system 700 may also include other peripheral output devices such as speakers, which may be connected through an output peripheral interface 794 or the like.

The system and method of the present disclosure may be embodied within a non-transitory computer-readable memory that includes instructions to implement the various operations described above. The instructions on the non-transitory computer-readable memory may be specially designed for the implementation of the system and method of the present disclosure or they may be any one of a variety of types of instructions known by those skilled in the art. Examples of a non-transitory computer-readable memory include, but are not limited to CD ROM discs, DVD discs, magneto-optical media such as optical disks, read-only memory (ROM), random access memory (RAM), flash memory, and hard disk drives.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated.

What is claimed is:

1. A system for identifying spatially and temporally distributed phase deviations within a sample under evaluation, comprising:
    a magnetic resonance imaging machine including a birdcage coil and a magnetic resonance machine radio frequency generator, wherein the magnetic resonance imaging machine applies a main magnetic field to the sample under evaluation within the magnetic resonance imaging machine, and wherein the birdcage coil comprises a plurality of orthogonal coil sets each comprising a coil B and a coil A, wherein an angle $\alpha$ between each coil B of the plurality and an axis orthogonal to the main magnetic field is different;
    an induction component configured to induce spatially and temporally ordered phase deviations of the transverse magnetization within the sample under evaluation;
    a computer system connected to the magnetic resonance imaging machine, wherein the computer system is configured to:
    receive a first voltage from a coil A of one of the orthogonal coil sets of the plurality;
    receive a second voltage from a coil B of the one of the orthogonal coils of the plurality;
    receive an output of the magnetic resonance machine radio frequency generator and phase-shift the output to a first and second phase-shifted voltage;
    multiply the first voltage by the first phase-shifted voltage to generate a first result;
    multiply the second voltage by the second phase-shifted voltage to generate a second result;
    sum the first and second results to generate a spatial Fourier transform of a Feature Space representing an original native data set of the sample under evaluation produced by the magnetic resonance imaging machine without the induction of the spatially and temporally ordered phase deviations;
    apply an inverse Fourier Transform to the spatial Fourier transform of the Feature Space representing the original native data set to generate a Feature Space which is the original native data set;
    multiply the first voltage by the second phase-shifted voltage to generate a third result;
    multiply the second voltage by the first phase-shifted voltage and invert the result to generate a fourth result;
    sum the third and fourth results to generate a spatial Fourier transform of an Aberrational Feature Space representing the product everywhere of the original native data set and the induced spatially and temporally ordered phase deviations;
    apply a deconvolution algorithm to the spatial Fourier transform of the Aberrational Feature Space and the spatial Fourier transform of the Feature Space to generate a fifth result;
    apply an inverse Fourier Transform to the fifth result to generate a Phase Aberration Space which is the data set of the spatially and temporally ordered phase deviations;
    generate at least one image using the Feature Space which is the original native data set; and
    generate at least one image using the Phase Aberration Space.

2. A method of identifying spatially and temporally distributed phase deviations within a sample under evaluation by a magnetic resonance imaging machine with a birdcage coil, wherein the birdcage coil comprises a plurality of orthogonal coil sets each comprising a coil B and a coil A, wherein an angle $\alpha$ between each coil B of the plurality and an axis orthogonal to the main magnetic field is different and a magnetic resonance machine radio frequency generator, comprising:
    applying a main magnetic field to the sample under evaluation by the magnetic resonance imaging machine;
    inducing spatially and temporally ordered phase deviations of the transverse magnetization within the sample under evaluation within the magnetic resonance imaging machine;
    receiving a first voltage from a coil A of one of the orthogonal coil sets of the plurality;
    receiving a second voltage from a coil B of the one of the orthogonal coil sets of the plurality;
    receiving an output of the magnetic resonance machine radio frequency generator and phase-shifting the output to a first and second phase-shifted voltage;
    multiplying the first voltage by the first phase-shifted voltage to generate a first result;
    multiplying the second voltage by the second phase-shifted voltage to generate a second result;
    summing the first and second results to generate a spatial Fourier transform of a Feature Space representing an original data set of the sample under evaluation produced by the magnetic resonance imaging machine without the induction of the spatially and temporally ordered phase deviations;
    applying an inverse Fourier Transform to the spatial Fourier transform of the Feature Space representing the original native data set to generate a Feature Space which is the original native data set;
    multiplying the first voltage by the second phase-shifted voltage to generate a third result;
    multiplying the second voltage by the first phase-shifted voltage and inverting the result to generate a fourth result;
    summing the third and fourth results to generate a spatial Fourier transform of an Aberrational Feature Space representing the product everywhere of the original native data set and the induced spatially and temporally ordered phase deviations;
    applying a deconvolution algorithm to the spatial Fourier transform of the Aberrational Feature Space and the spatial Fourier transform of the Feature Space to generate a fifth result;
    applying an inverse Fourier Transform to the fifth result to generate a Phase Aberration Space which is the data set of the spatially and temporally ordered phase deviations; and
    generating at least one of an image using the Feature Space which is the original native data set or an image using the Phase Aberration Space.

3. A system for identifying spatially and temporally distributed phase deviations within a sample under evaluation, comprising:
    a magnetic resonance imaging machine including at least one quadrature coil set and a magnetic resonance machine radio frequency generator, wherein the magnetic resonance imaging machine applies a main magnetic field to the sample under evaluation within the magnetic resonance machine;

an induction component configured to induce spatially and temporally ordered phase deviations of the transverse magnetization within the sample under evaluation;

a computer system connected to the magnetic imaging resonance machine, wherein the computer system is configured to:

receive a first voltage from the at least one quadrature coil set;

receive a second voltage from the at least one quadrature coil set;

receive an output of the magnetic resonance machine radio frequency generator and phase-shift the output to a first and second phase-shifted voltage;

multiply the first voltage by the first phase-shifted voltage to generate a first result;

multiply the second voltage by the second phase-shifted voltage to generate a second result;

sum the first and second results to generate a spatial Fourier transform of a Feature Space representing an original native data set of the sample under evaluation produced by the magnetic resonance imaging machine without the induction of the spatially and temporally ordered phase deviations;

apply an inverse Fourier Transform to the spatial Fourier transform of the Feature Space representing the original native data set to generate a Feature Space which is the original native data set;

multiply the first voltage by the second phase-shifted voltage to generate a third result;

multiply the second voltage by the first phase-shifted voltage and invert the result to generate a fourth result;

sum the third and fourth results to generate a spatial Fourier transform of an Aberrational Feature Space representing the product everywhere of the original native data set and the induced spatially and temporally ordered phase deviations;

apply a deconvolution algorithm to the spatial Fourier transform of the Aberrational Feature Space and the spatial Fourier transform of the Feature Space to generate a fifth result;

apply an inverse Fourier Transform to the fifth result to generate a Phase Aberration Space which is the data set of the spatially and temporally ordered phase deviations;

generate at least one image using the Feature Space which is the original native data set; and generate at least one image using the Phase Aberration Space.

* * * * *